(12) United States Patent
Rising et al.

(10) Patent No.: US 7,193,717 B2
(45) Date of Patent: Mar. 20, 2007

(54) SYSTEM AND METHOD FOR ANALYZING MICROBIAL GROWTH

(75) Inventors: Peter Rising, Brightwaters, NY (US); John Remmer, Oakdale, NY (US)

(73) Assignee: Industrial Municipal Equipment, Inc., Eldersburg, MD (US)

( * ) Notice: Subject to any disclaimer, the term of this patent is extended or adjusted under 35 U.S.C. 154(b) by 358 days.

(21) Appl. No.: 10/859,837

(22) Filed: Jun. 3, 2004

(65) Prior Publication Data
US 2005/0270534 A1 Dec. 8, 2005

(51) Int. Cl.
*G01N 21/84* (2006.01)
(52) U.S. Cl. ............. 356/432; 356/408; 356/436
(58) Field of Classification Search ........ 356/432–436, 356/440–446, 408; 422/82.09; 250/228
See application file for complete search history.

(56) References Cited
U.S. PATENT DOCUMENTS 5,013,155 A * 5/1991 Rybak .................. 356/408
6,493,085 B1 12/2002 Pfeifer et al.
6,762,842 B2 7/2004 Pfeifer et al.
6,768,549 B1 7/2004 Pfeifer et al.
2006/0066858 A1* 3/2006 Jaunakais et al. .......... 356/436

\* cited by examiner

*Primary Examiner*—Layla G. Lauchman
*Assistant Examiner*—Tri Ton
(74) *Attorney, Agent, or Firm*—Nathaniel Wallace

(57) ABSTRACT

A liquid testing system includes a first well for receiving a sample to be tested, a first light, having a first wavelength, for illuminating the first well, and a second light, having a second wavelength, for illuminating the first well. The liquid testing system further includes a light control, coupled to the first light and the second light, for selecting one of the first light or the second light to illuminate the first well, a light detector receiving light passing into the first well, and a processor, coupled to the light control and the light detector, for determining a light characteristic of the sample over time.

21 Claims, 6 Drawing Sheets

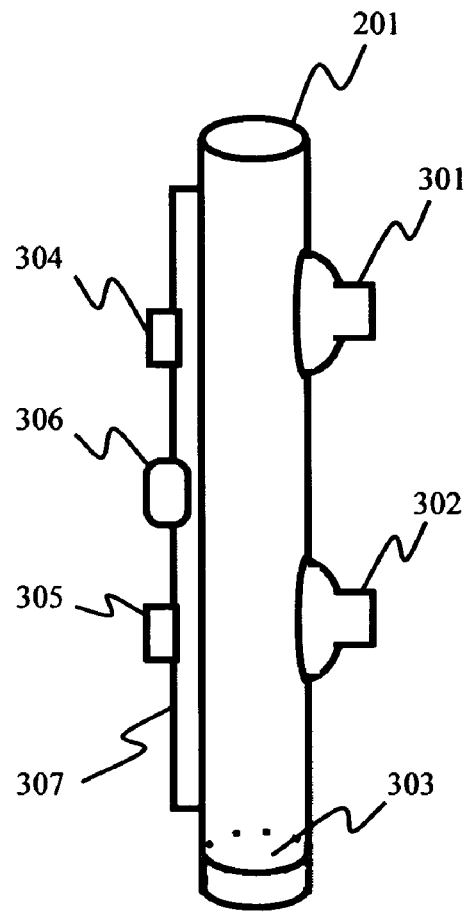
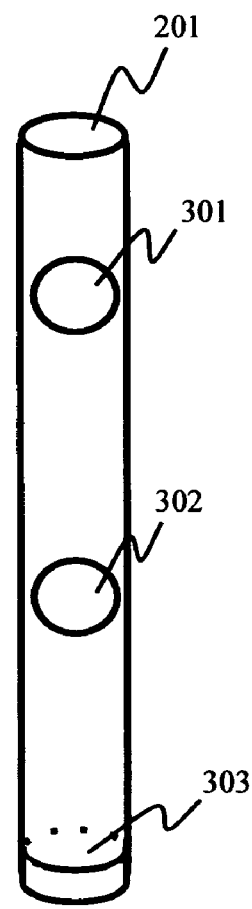
FIGURE 3A
FIGURE 3B
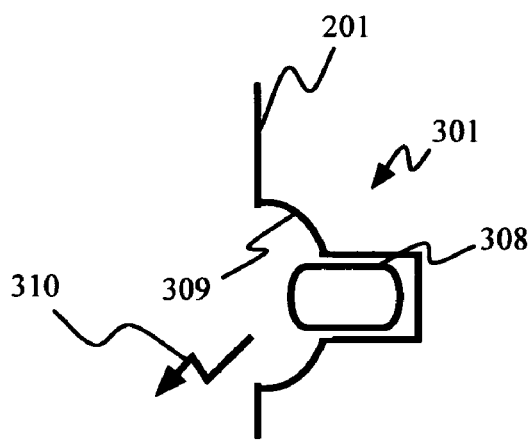
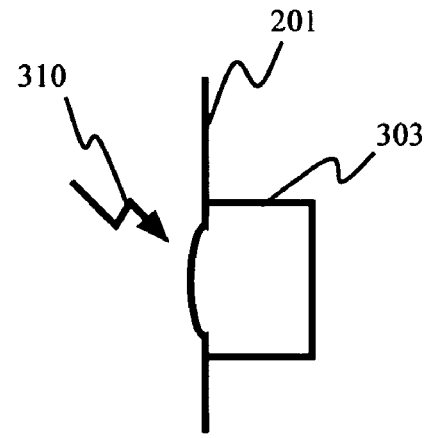
FIGURE 3C
FIGURE 3D

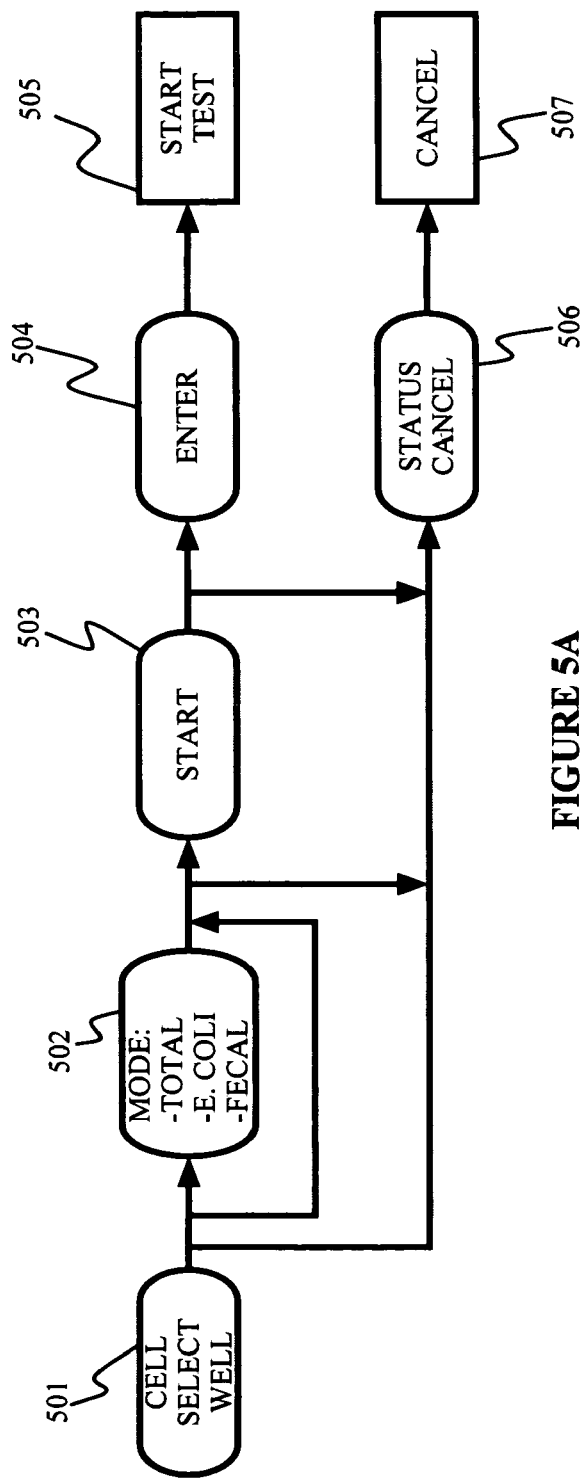
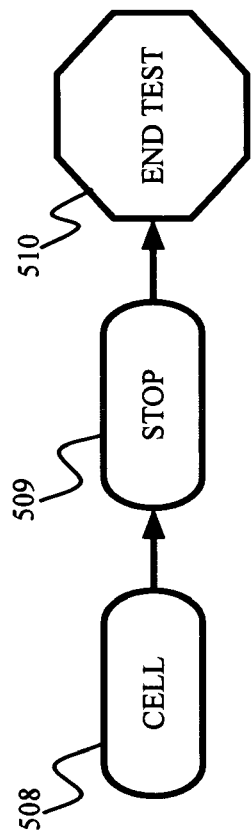
FIGURE 5A
FIGURE 5B

SYSTEM AND METHOD FOR ANALYZING MICROBIAL GROWTH

BACKGROUND OF THE INVENTION

1. Field of the Invention

The present invention relates to determining the presence of microbes, and more particularly to a system and method for automatically analyzing microbial growth in an aqueous sample.

2. Discussion of Related Art

Accuracy and repeatability may be important in establishing significant results in the study of microbes. Methods of analyzing microbial growth may involve human monitoring of test equipment in laboratory and field settings. Human control and interpretation of an analysis may result in inaccurate test results.

Therefore, a need exists at least for a system and/or method for automatic analysis of a sample for the presence of microbes.

SUMMARY OF THE INVENTION

According to an embodiment of the present disclosure, a liquid testing system includes a first well for receiving a sample to be tested, a first light source for illuminating the first well with light having a first wavelength, and a second light for illuminating the first well with light having a second wavelength. The liquid testing system further includes a light control, coupled to the first light source and the second light source, for selecting one of the first light source or the second light source to illuminate the first well, a light detector receiving light passing through the first well, and a processor, coupled to the light control and the light detector, for determining a light characteristic of the sample over time.

The liquid testing system includes a second well for receiving a second sample to be tested, the second well being selectively exposed to one of the light having the first wavelength or the light having the second wavelength. The liquid testing system further includes a second well for receiving a second sample to be tested, the processor for implementing different tests in the first well and the second well simultaneously. The liquid testing system includes a second well for receiving a second sample to be tested, a third light for illuminating the second well with light having the first wavelength, and a fourth light for illuminating the second well with light having the second wavelength, the second well being selectively exposed to one of the light having the first wavelength or the light having the second wavelength according to the light control.

The liquid testing system includes an input device for selecting a mode of the liquid testing system. The mode is a species-specific test. The mode is an end-of-test parameter. The mode is a temperature mode.

The liquid testing system includes a heating element for heating the first well, a heat control coupled to the heating element for controlling the heating element, and a thermal sensor for monitoring a temperature of the first well. The processor is coupled to the thermal sensor and heat control, and receives a signal of the first well from the thermal sensor and controls the heat control for maintaining a predetermined temperature of the first well, wherein the signal corresponds to the temperature of the first well.

The light characteristic is at least one of color, color intensity, opacity, and/or excitation.

According to an embodiment of the present disclosure, a method for testing an aqueous solution includes obtaining the aqueous solution, selecting a test mode simultaneously defining a light wavelength and a temperature profile, initiating a test by exposing the aqueous solution to the light wavelength and the temperature profile, monitoring transmission of light through the aqueous solution, the light having the light wavelength, and determining a presence of a biologic component of the aqueous solution according to the transmission of light through the aqueous solution.

The method includes setting an end-of-test mode for automatically ending the test. The end-of-test mode ends the test upon one of an elapsed time and determining a predetermined parameter of the aqueous solution.

The method further includes delaying the monitoring of the transmission of light for a predetermined time after initiating the test.

According to an embodiment of the present disclosure, an ampoule well for receiving a test ampoule including a aqueous solution includes a first light source coupled to a sidewall of the ampoule well for illuminating the ampoule well, the light having a first predetermined wavelength, a second light source coupled to the sidewall of the ampoule well for illuminating the ampoule well, the light having a second predetermined wavelength, and a photodetector positioned at an end of the ampoule well for detecting light of the first light source and/or the second light source passing through the aqueous solution.

The first light source is positioned at a distance from the photodetector according to a transmission of light having the first predetermined wavelength through a known aqueous solution comprising a reagent in the test ampoule.

The photodetector has a sensitivity to a wavelength according to a reagent in the test ampoule, wherein the reagent changes color over time.

At least one of the first light source and the second light source includes a reflector coupled to the sidewall of the ampoule well for directing light into the ampoule well, wherein the sidewall of the ampoule well comprises an opening for receiving the light.

The ampoule well includes a heating element, a thermal sensor, and a heat conducting, electrically insulating, material positioned between the heating element and the ampoule well and the thermal sensor and the ampoule well, the heat conducting, electrically insulating, material coupling the heating element to the ampoule well and the thermal sensor to the ampoule well.

BRIEF DESCRIPTION OF THE DRAWINGS

Preferred embodiments of the present invention will be described below in more detail, with reference to the accompanying drawings:

FIGS. 3A and 3B are illustrations of an ampoule well according to an embodiment of the present disclosure;

FIG. 3C is an illustration of a light source according to an embodiment of the present disclosure;

FIG. 3D is an illustration of a light detection means according to an embodiment of the present disclosure;

FIG. 5A is a flow diagram of a method for selecting a mode according to an embodiment of the present disclosure;

FIG. 5B is a flow diagram of a method for ending a test according to an embodiment of the present disclosure;

DETAILED DESCRIPTION OF PREFERRED EMBODIMENTS

A system for performing automatic analysis of microbial growth in an aqueous sample includes an incubator and an analyzer. The incubator maintains a predetermined temperature profile over time. The analyzer monitors a characteristic of the sample over time. The sample may be mixed with a reagent, wherein the reagent reacts to a biologic component of the sample.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 1:
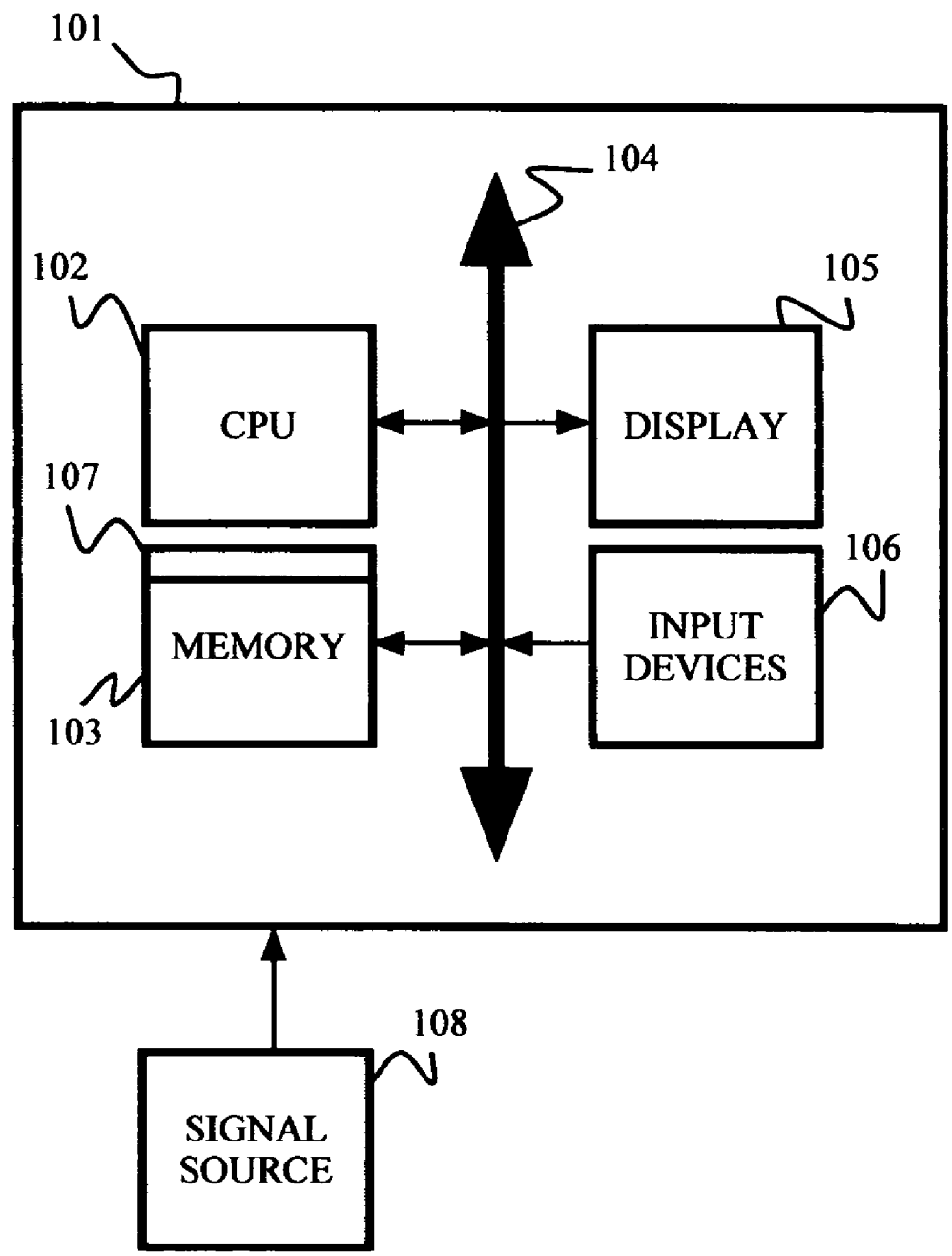
FIG. 1 is an illustration of a test system according to an embodiment of the present disclosure.

Referring to FIG. 1, according to an embodiment of the present invention, a testing system 101 for implementing the present invention can comprise, inter alia, a central processing unit (CPU) 102, a memory 103 and an input/output (I/O) interface 104. The testing system 101 may be coupled through the I/O interface 104 to a display 105 and input device 106 such as a keypad and/or mouse. The support circuits can include circuits such as cache, power supplies, clock circuits, and a communications bus. The memory 103 can include random access memory (RAM), read only memory (ROM), disk drive, tape drive, etc., or a combination thereof. The present invention can be implemented as a routine 107 that is stored in memory 103 and executed by the CPU 102 to process the signal from the signal source 108. As such, the testing system 101 is a general-purpose computer system that becomes a specific purpose computer system when executing the routine 107 of the present invention.

The testing platform 101 may include an operating system and microinstruction code. The various processes and functions described herein may either be part of the microinstruction code or part of the application program (or a combination thereof), which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Figure 2:
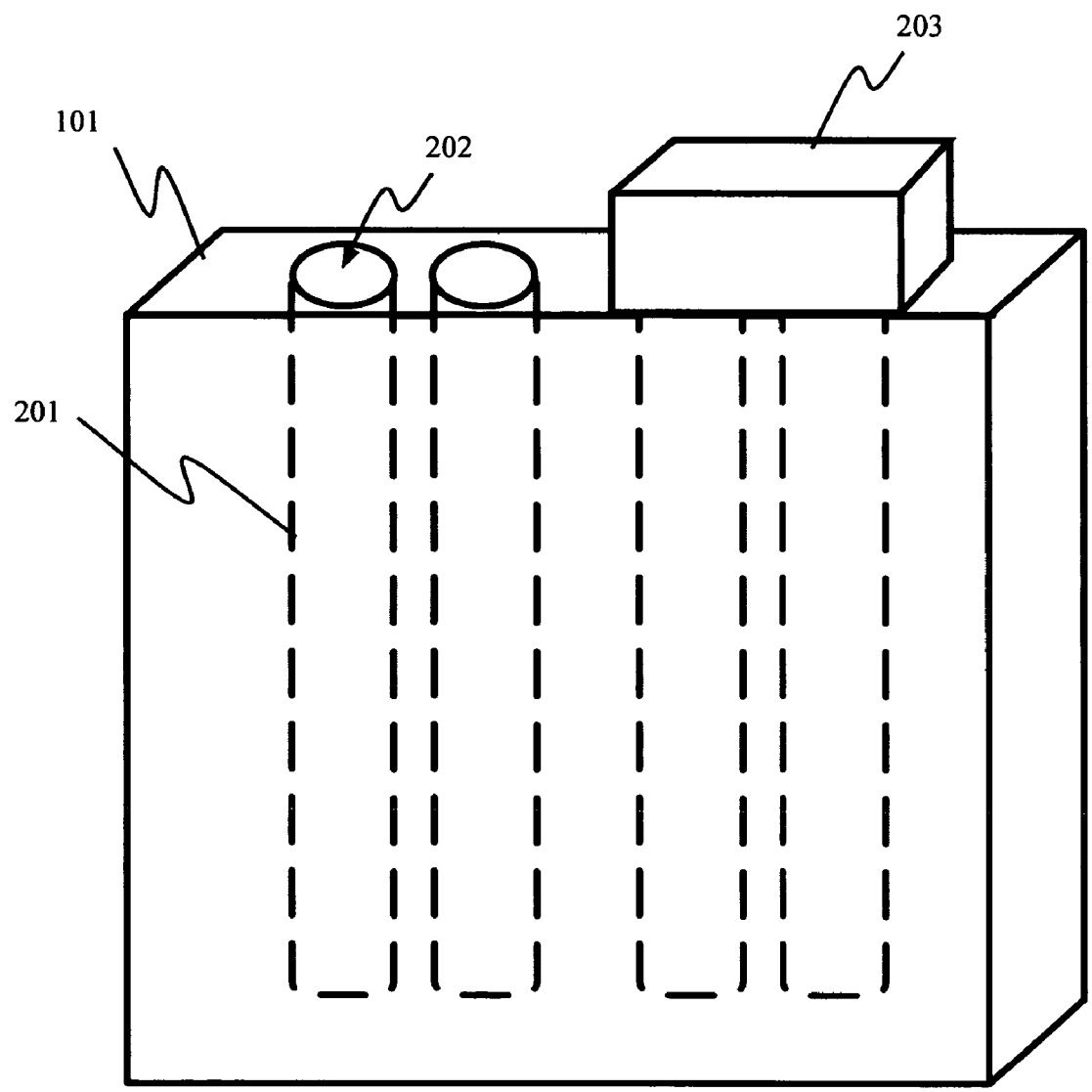
FIG. 2 is an illustration of a test system according to an embodiment of the present disclosure.

Referring to FIG. 2, a system 101 includes one or more ampoule wells 201. The ampoule wells 201 may be formed of a metal such as Aluminum. An interior surface 202 of the ampoule wells 201 may be polished for reflecting light. The interior surface 202 of the ampoule wells 201 may be covered with a reflective material such as chrome or Mylar® tape for improved light reflection within the wells. Further, the interior surface 202 may be selectively treated, e.g., an upper ⅓ of the well is chromed.

During testing the ampoule wells 201 are heated to an incubation temperature. A timer monitors the time of the incubation temperature or temperature profile. The timer may be software or hardware based, or a combination of software and hardware.

Referring to FIGS. 3A and 3B, each ampoule well 201 includes at least one light source 301. The light source 301 is mounted to a sidewall of the ampoule well 201, wherein the sidewall includes an opening allowing light to pass into the ampoule well 201. The light source 301 is mounted to the ampoule well 201 using an adhesive, a clip, a press fit or the like. The location of the light source 301 on the sidewall improves the reliability of a test by reducing the effects of light transmission through an end of a test ampoule that may include bubbles in the sample, a meniscus, variable thicknesses of a shoulder of the test ampoule, etc. Ambient light is blocked from entering the ampoule well 201 by, for example, a cap 203 or cork over an opening of the ampoule well for receiving an ampoule (see FIG. 2).

Where more than one light source is provided, different light sources may provide different portions or wavelengths of the electromagnetic spectrum. The electromagnetic spectrum includes, from longest wavelength to shortest: radio waves, microwaves, infrared, optical, ultraviolet, X-rays, and gamma-rays. For example, a first light source 301 may be a full optical spectrum light source (e.g., wavelengths between about 7000 and about 4000 Angstroms) and a second light source 302 may be an ultraviolet light source (e.g., one or more wavelengths between about 4000 and about 10 Angstroms). Other wavelengths of light may be provided. A desired wavelength may be achieved through selection of a lamp or light emitted diode, a color filter, a filter grating, or the like. The filter is positioned to allow light of the desired wavelength into the ampoule well 201. Likewise, a filter may be used to block an undesirable wavelength of light.

Depending on the detection means, other characteristics of the electromagnetic spectrum may be considered in analyzing a sample including changes frequency, e.g., the number of oscillations per second of an electromagnetic wave, and bandwidth, e.g., the range of frequencies that make up a signal as light passes through the sample.

For a given test, one light source may be selected wherein a second light source is turned off. Light from the selected light source(s) illuminates the ampoule well 201 and is detected by a detection means 303, such as a photodetector located in a bottom portion of the ampoule well 201. The detection means 303 may be positioned at a bottom of the ampoule well 201 or on a sidewall of the ampoule well 201, wherein the detection means 303 is exposed to the inside of the ampoule well 201 for receiving light 310 from one or more light sources (see FIG. 3D).

The light source(s) and detection means 303 may by tuned to a specific reaction/reagent, for example, where a reagent turns from yellow to orange in the presence of a certain microbe the light source may emit light in a blue wavelength and the detection means may be tuned to be sensitive to the green wavelength. Thus, as the reagent turns from yellow to orange, the transmission of the light through the sample would decrease and be detected.

An ampoule or vial, such as a sealed indicator vial, containing a sample of interest is placed in the ampoule well 201, such that light from a selected light source is transmitted through the sample of interest to the detection means 303. The ampoule or vial is fabricated from glass or another translucent material. The ampoule or vial may be, for example, a sealed indicator vial, a test tube, a pipette, or the like.

The temperature of the sample of interest may be controlled via one or more heating elements 304 and 305 and a thermal sensor 306. The heating element 304 and thermal sensor 306 may be elements of a circuit board to which the ampoule well is secured. The heating elements 304–305 are coupled to the ampoule well 201 by a heat conducting/electrically insulating material 307 such as Silicon rubber. The thermal sensor 306 determines a temperature of the ampoule well 201, which corresponds to an incubation temperature of an ampoule disposed in the ampoule well 201. The temperature profile or incubation temperature may be controlled according to a target microbe being studied. For example, total Coliform and *Escherichia coli* may be incubated at a stable temperature of 35° C./95° F. Other microbes may be analyzed uses a variable temperature profile.

Referring to FIG. 3C, each light source, e.g., 301, comprises a light bulb 308, such as a light emitting diode, and a reflector 309. The ampoule well 201 and reflector 309 may be formed as a single piece or may be separate components, wherein the reflector 309 is mounted to the sidewall of the ampoule well 201. The light bulb 308 may be press-fit into the reflector, secured by adhesive, a clip, or the like. A shape of the reflector 309 directs light 310 from the light bulb 308 into the ampoule well 201. The location of a light source relative to a light detector may be determined according to a transmission quality of a particular light wavelength through a sample and a known quality of a reagent used with a particular light source. For example, a full optical spectrum light used in a test for total microbial growth may be positioned at about 2.60 inches from the light detector and an ultraviolet light source used in a test for Escherichia coli or a 4-methylumbelliferyl-β-D glucuronide (MUG) test may be positioned at about 1.50 inches from the light detector.

Figure 4:
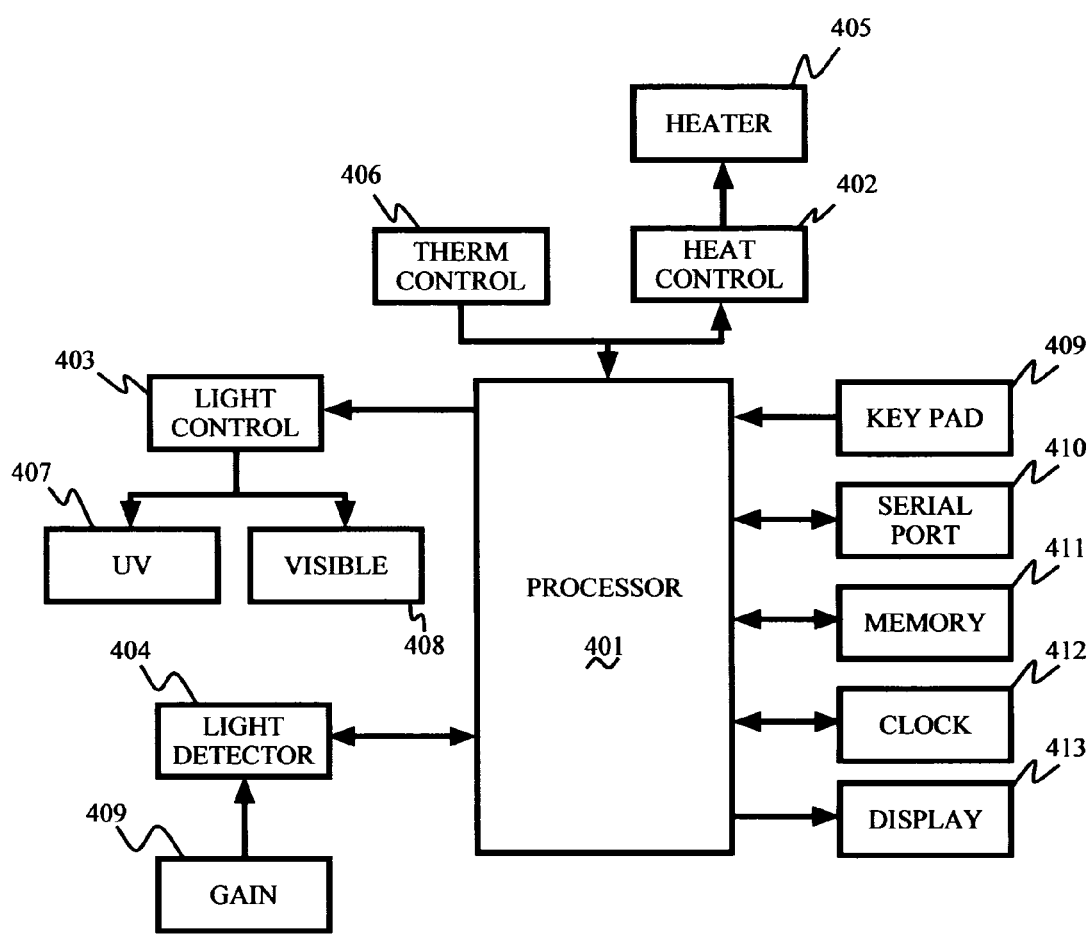
FIG. 4 is an illustration of a circuit according to an embodiment of the present disclosure.

Referring to FIG. 4, a control circuit of the system includes a processor 401 coupled to a heat control device 402, a light control device 403, and a light detection device 404. The heat control device 402 controls a heating element 405 for controlling an incubation temperature of an ampoule well and its contents. The processor 401 receives temperature information from a thermostat 406, which forms a control loop with the processor 401, heat control device 402 and heating element 405 for controlling the temperature of the ampoule well. The light control device 404 is coupled to a light source, such as an ultraviolet light 407 or a visible light 408. The light detection device 404 monitors light passing through the test ampoule and any contents therein. A gain control 409 can be adjusted to control a sensitivity of the light detection device 404. Light information is passed to the processor 401.

Individual wells of the system may be controlled using a well specific heat control 402 and light control 403. Multiple lights 407–408 may be provided for each well. Likewise, multiple heating elements 405 may be provided for each well. Thus, the same or different tests may be preformed in different wells simultaneously. For example, one or more temperature profiles can be run simultaneously. Further still, different light sources can be used for different ampoules. Thus, for example, a test for *Escherichia coli* can be performed in a first ampoule well and a test for fecal Coliform can be performed in a second ampoule well. Separate results may be provided for each test.

The processor 401 may be coupled to additional devices, including, for example, an input device 409, such as a keypad, a serial port 410, a memory device 411, a clock 412, and a display 413.

The temperature profile, e.g., the temperature at predetermined times during a test, may be controlled by the control circuit of FIG. 4 or a communications link to a processor. The processor may be, for example, a personal computer or a handheld device (e.g., a personal digital assistant (PDA)). The communications link may be embodied as a serial link, a universal serial bus (USB) connection, a Bluetooth wireless connection or the like.

Upon heating the sample to the incubation temperature, the time is noted. The light transmitted through the sample is monitored during the incubation period. Upon detecting a predetermined change in a characteristic of the light through the sample, an end point is determined. The characteristic may be, for example, at least one of color, color intensity, opacity, or excitation, e.g., fluorescence in ultraviolet light. The predetermined change may be, for example, a 25% decrease in light transmission through the sample or opacity. The change in the characteristic may be averaged over time to account for random variations in the characteristic. According to another example the test may be allowed to continue indefinitely.

According to one embodiment of the present description, a test sample may start as a pale pink and progress to a darkening red and the light source may be a clear green light emitted diode. For an *Escherichia coli*/fecal Coliform test, a blue wavelength light may be used. During the *Escherichia coli*/fecal Coliform test, an ultraviolet (e.g., 365 nM) response may be determined using a blue-green light. One skilled in the art would appreciate, in light of the present invention, that other characteristics may be determined and that different wavelengths of light may be used to make a given determination.

At the conclusion of the test, such as upon determining a predetermined increase in color intensity or upon a laboratory technician determining an end point, test results are stored or output. The output may include data points of color versus time, elapsed time for one or more tests, temperature of one or more ampoule wells, etc.

The output may be stored in a memory device, output to a computer monitor, output to an integrated display of the system, or by printer, among others.

The system includes hardware and/or software for controlling the analysis. More particularly, an electronics board includes a memory device such as an electrically erasable programmable read-only memory (EEPROM) or flash type memory and processor. The system may include a communications port, such as an RS232 port. Commands may be transmitted via the communications port. For example, a command set permits retrieval of raw data from the memory. Test from each test mode, status, temperature, elapsed time, and light level. Additional parameters may be monitored, such as initiation, test progress/phase, and termination of tests.

The system is adapted to permit continuation of test after power supply interruption, wherein, upon power restoration, the test status of the cells is recalled from a memory device and the test continued. The power supply may be a plug-in power module, a battery system, or direct current (DC) adapter systems such as used with an automobile accessory power sources.

Different tests may be performed under various conditions. For example, a test may be performed using 365 nm ultraviolet light and a test for fluorescence. The system may include an ultraviolet light emitting diode built into an ampoule well and a test the presence of fecal Coliform using MUG.

The present disclosure incorporates by reference, in the entirety, U.S. Pat. No. 5,159,799, filed Oct. 24, 1991, entitled VIAL WITH POWDERED REAGENT, U.S. Pat. No. 5,550,032, filed May 27, 1994, entitled BIOLOGICAL ASSAY FOR MICROBIAL CONTAMINATION, and U.S. Pat. No. 5,935,799, filed Dec. 10, 1997, entitled BIOLOGICAL ASSAY FOR MICROBIAL CONTAMINATION.

The system and method maintain incubation of vials at predetermined temperatures. Sample characteristics, such as color and/or obscurity, of the sample are determined continuously or periodically for a predetermined time or the duration of the test. For example, a color of a sample may be determined every minute for the first 20 minutes of a test.

The system and method determine and display microbial concentrations over a predetermined time, e.g., 9 hours, 24 hours, or 80 hours.

A method for analysis of microbial presence and/or growth includes incubation of a sample at a predetermined temperature profile. The profile includes temperature and time variables. A profile may be a static temperature for an indefinite time. Sample parameters, such as color or obscurity, are monitored during the profile. The parameters may be determined periodically or continuously. The parameter of the sample may include one or more of time, temperature, and color/turbidity of a sample. Additional parameters are contemplated. Based on the parameters of the sample, such as change in color in relation to time, a tested condition of the sample, such as the presence of a particular microbe, can be determined.

The system and/or method may perform tests for a variety of domains. For example, domains may include determining biomass in cooling tower waters, determining microbial activity in sewage treatment systems, testing for the presence of sulfur bacteria in cooling waters of fuel storage tanks and microbial presence in fine line water systems.

The testing system can determine results according to a program code. Results may be determined based on raw data as interpreted by a human or output to a processor.

The system and method may take a variety of inputs for controlling functions. Referring to FIGS. 5A and 5B, examples of these inputs are shown. For example, a user may select a cell 501 and a mode 502, and a sequence of inputs, e.g., state 503 and enter 504, to begin a test 505. The mode selection 502 may include a display of available modes. The modes may include selections for species-specific test, end-of-test modes, temperature parameters, etc. For example, a group of modes may be displayed for species-specific tests including a total microbial activity test, a test for *Escherichia coli*, or a test for fecal Coliform. The system and method may default to a mode of a previous test. A test may be cancelled before or during the test. A test may be cancelled before a test has begun by selecting a status 506, e.g., cancel test, which cancel input settings and display a current status 507. A test may be cancelled during the test by selecting a cell 508 having the test to be cancelled and selecting to stop 509 the test. The test ends 510 upon selecting to stop 509 the test.

The start of a test 505 may be delayed for a predetermined time. The delay, for example, about 30–60 minutes, reduces the presence of variables in the sample. For example, variables may include allow for the elimination of bubbles, for a predetermined temperature of the sample to be achieved, for solids in the sample to dissolve, chemical mixing, allowing early outgassing to take place, and to allow sediment to fall.

Figure 6:
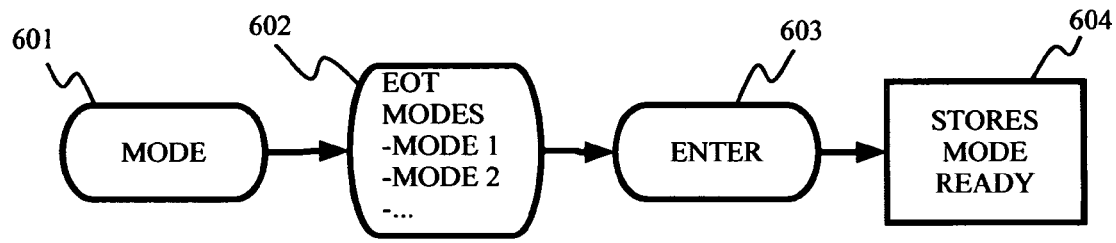
FIG. 6 is a flow diagram of a method for selecting an end-of-test mode according to an embodiment of the present disclosure.

Referring to FIG. 6, a user may select a mode for determining an end-of-test (EOT) parameter. The end-of-test parameter may include, for example, a predetermined time such as 30 minutes, or a predetermined color/turbidity measurement. A mode input 601 is used to select an end-of-test mode 602. Upon determining a desired mode, a user may enter 603 and store the mode 604 to be implemented in a test.

Figure 7:
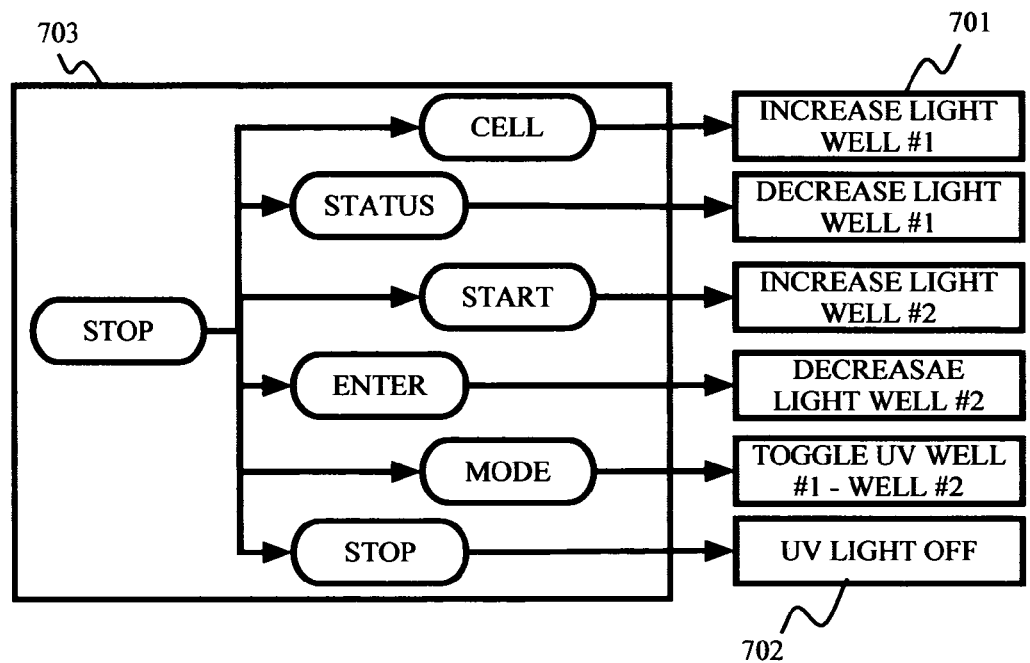
FIG. 7 is a flow diagram of a method for controlling individual wells according to an embodiment of the present disclosure.

In addition to providing selections for modes, individual wells of the system may be controlled. For example, light levels 701 and light types 702 may be controlled according to a user input 703 (see FIG. 7). One of ordinary skill in the art would appreciate that selections may be made using any of a variety of input. For example, individual buttons or a combination or sequence of buttons to make certain selections. Another example includes a graphical user interface for entering input, such as that implemented by an operating system running on a personal computer for making selections.

Having described embodiments for a system and method of determining the presence of a biologic agent, it is noted that modifications and variations can be made by persons skilled in the art in light of the above teachings. It is therefore to be understood that changes may be made in the particular embodiments of the invention disclosed which are within the scope and spirit of the invention.

What is claimed is:

1. A liquid testing system comprising:
   a first well for receiving a sample to be tested;
   a first light source for illuminating the first well with light having a first wavelength;
   a second light source for illuminating the first well with light having a second wavelength;
   a light control coupled to the first light source and second light source, for selecting one of the first light source or the second light source to illuminate the first well;
   a light detector receiving light passing through the first well; and
   a processor, coupled to the light control and the light detector, for determining a light characteristic of the sample over time; and
   a second well for receiving a second sample to be tested, the processor for implementing different tests in the first well and the second well simultaneously.

2. The liquid testing system of claim 1, further comprising a second well for receiving a second sample to be tested, the second well being selectively exposed to one of the light having the first wavelength or the light having the second wavelength.

3. The liquid testing system of claim 1, further comprising:
   a second well for receiving a second sample to be tested;
   a third light source for illuminating the second well with light having the first wavelength; and
   a fourth light source for illuminating the second well with light having the second wavelength, the second well being selectively exposed to one of the light having the first wavelength or the light having the second wavelength according to the light control.

4. The liquid testing system of claim 1, further comprising an input device for selecting a mode of the liquid testing system.

5. The liquid testing system of claim 4, wherein the mode is a species-specific test.

6. The liquid testing system of claim 4, wherein the mode is an end-of-test parameter.

7. The liquid testing system of claim 4, wherein the mode is a temperature mode.

8. The liquid testing system of claim 1, further comprising:
a heating element for heating the first well;
a heat control coupled to the heating element for controlling the heating element; and
a thermal sensor for monitoring a temperature of the first well, the processor coupled to the thermal sensor and heat control, receiving a signal of the first well from the thermal sensor and controlling the heat control for maintaining a predetermined temperature of the first well, wherein the signal corresponds to the temperature of the fist well.

9. The liquid testing system of claim 1, wherein the light characteristic is at least one of color, color intensity, opacity, and excitation.

10. A method for testing an aqueous solution comprising:
obtaining the aqueous solution;
selecting a test mode simultaneously defining a light wavelength and a temperature profile;
setting an end-of-test mode for automatically ending the test;
initiating a test by exposing the aqueous solution to the light wavelength and the temperature profile;
monitoring transmission of light through the aqueous solution, the light having the light wavelength; and
determining a presence of a biologic component of the aqueous solution according to the transmission of light through the aqueous solution.

11. The method of claim 10, wherein the end-of-test mode ends the test upon one of an elapsed time and determining a predetermined parameter of the aqueous solution.

12. The method of claim 10, further comprising delaying the monitoring of the transmission of light for a predetermined time after initiating the test.

13. An ampoule well for receiving a test ampoule comprising an aqueous solution, the ampoule well comprising:
a first light source coupled to a sidewall of the ampoule well for illuminating the ampoule well, the light having a first predetermined wavelength;
a second light source coupled to the sidewall of the ampoule well for directing light into the ampoule well, the light having a second predetermined wavelength; and
a photodetector positioned at an end of the ampoule well for detecting light of the first light source and/or the second light source passing through the aqueous solution.

14. The ampoule well of claim 13, wherein the first light source is positioned at a distance from the photodetector according to a transmission of light having the first predetermined wavelength through a known aqueous solution comprising a reagent in the test ampoule.

15. The ampoule well of claim 13, wherein the photodetector has a sensitivity to a wavelength according to a reagent in the test ampoule, wherein the reagent changes color over time.

16. The ampoule well of claim 13, wherein at least one of the first light source and the second light source comprises a parabolic reflector coupled to the sidewall of the ampoule well for directing light into the ampoule well, wherein the sidewall of the ampoule well comprises an opening for receiving the light.

17. The ampoule well of claim 13, further comprising:
a heating element;
a thermal sensor; and
a heat conducting, electrically insulating, material positioned between the heating element and the ampoule well and the thermal sensor and the ampoule well, the heat conducting, electrically insulating material coupling the heating element to the ampoule well and the thermal sensor to the ampoule well.

18. A liquid testing system comprising:
a first well for receiving a sample to be tested;
a first light source for illuminating the first well with light having a first wavelength;
a second light source for illuminating the first well with light having a second wavelength;
a light control coupled to the first light source and the second light source, for selecting one of the first light source or the second light source to illuminate the first well;
a light detector receiving light passing through the first well;
a processor, coupled to the light control and the light detector, for determining a light characteristic of the sample over time; and
an input device for selecting a mode of the liquid testing system, wherein the mode is a species-specific test.

19. A liquid testing system comprising:
a first well for receiving a sample to be tested;
a first light source for illuminating the first well with light having a first wavelength;
a second light source for illuminating the first well with light having a second wavelength;
a light control coupled to the first light source and the second light source, for selecting one of the first light source or the second light source to illuminate the first well;
a light detector receiving light passing through the first well;
a processor, coupled to the light control and the light detector, for determining a light characteristic of the sample over time; and
an input device for selecting a mode of the liquid testing system, wherein the mode is an end-of-test parameter.

20. A liquid testing system comprising:
a first well for receiving a sample to be tested;
a first light source for illuminating the first well with light having a first wavelength;
a second light source for illuminating the first well with light having a second wavelength;
a light control coupled to the first light source and the second light source, for selecting one of the first light source or the second light source to illuminate the first well;
a light detector receiving light passing through the first well;
a processor, coupled to the light control and the light detector, for determining a light characteristic of the sample over time; and
an input device for selecting a mode of the liquid testing system, wherein the mode is a temperature mode.

21. A method for testing an aqueous solution comprising:
obtaining the aqueous solution;
selecting a test mode simultaneously defining a light wavelength and a temperature profile;

initiating a test by exposing the aqueous solution to the light wavelength and the temperature profile;
delaying the monitoring of the transmission of light for a predetermined time after initiating the test;
monitoring transmission of light through the aqueous solution, the light having the light wavelength; and determining a presence of a biologic component of the aqueous solution according to the transmission of light through the aqueous solution.

\* \* \* \* \*